(12) United States Patent
Ishinari (10) Patent No.: US 12,396,690 B2
(45) Date of Patent: Aug. 26, 2025

(54) CONTROL APPARATUS, RADIATION IMAGING APPARATUS, AND RADIATION IMAGING SYSTEM

(71) Applicant: CANON KABUSHIKI KAISHA, Tokyo (JP)

(72) Inventor: Yutaka Ishinari, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 133 days.

(21) Appl. No.: 18/357,877

(22) Filed: Jul. 24, 2023

(65) Prior Publication Data

US 2024/0023913 A1 Jan. 25, 2024

(30) Foreign Application Priority Data

Jul. 25, 2022 (JP) .................... 2022-117631

(51) Int. Cl.
*A61B 6/00* (2024.01)
*H01Q 9/04* (2006.01)
*G01T 7/00* (2006.01)

(52) U.S. Cl.
CPC ............. *A61B 6/44* (2013.01); *H01Q 9/0414* (2013.01); *G01T 7/00* (2013.01)

(58) Field of Classification Search
CPC .......... A61B 6/44; A61B 6/54; A61B 6/4283; A61B 6/563; A61B 6/56; A61B 6/40; A61B 6/42; H01Q 9/0414; H01Q 1/38; H01Q 3/24; G01T 7/00
See application file for complete search history.

(56) References Cited

U.S. PATENT DOCUMENTS

| | | | | |
|---|---|---|---|---|
| 2010/0208871 A1* | 8/2010 | Tanabe | .................. | A61B 6/548 378/189 |
| 2010/0246757 A1* | 9/2010 | Liu | ........................ | G03B 42/02 378/19 |
| 2010/0330940 A1* | 12/2010 | Sheynblat | ............ | H04B 7/0608 455/277.1 |

FOREIGN PATENT DOCUMENTS

| | | |
|---|---|---|
| JP | 2010197679 A | 9/2010 |
| JP | 2018164161 A | 10/2018 |
| JP | 2021069805 A | 5/2021 |
| JP | 2021191390 A | 12/2021 |
| WO | 2006101231 A | 9/2006 |

* cited by examiner

*Primary Examiner* — Kiho Kim
(74) *Attorney, Agent, or Firm* — Canon U.S.A., Inc. IP Division (57) ABSTRACT

A control apparatus, that controls a radiation imaging apparatus in a radiation imaging system. where the radiation imaging apparatus includes a plurality of antennas for wireless local area network (LAN) communication used in transmitting a radiation image obtained by radiation imaging, obtains information about the radiation imaging system, determines at least one antenna from among the plurality of antennas as an antenna to be used for the wireless LAN communication based on the obtained information, and transmits information about the antenna to be used to the radiation imaging apparatus.

17 Claims, 5 Drawing Sheets

CONTROL APPARATUS, RADIATION IMAGING APPARATUS, AND RADIATION IMAGING SYSTEM

BACKGROUND

Field

The present disclosure relates to a control apparatus, a radiation imaging apparatus, and a radiation imaging system.

Description of the Related Art

In recent years, radiation imaging apparatuses using a flat panel detector including a two-dimensional array of solid-state image sensors made of amorphous silicon or monocrystalline silicon have been widely used as imaging apparatuses for radiological medical image diagnosis and non-destructive inspection.

These radiation imaging apparatuses can obtain an image by accumulating signal charges generated in the respective pixels based on the detected amount of radiation, reading the charges, and performing analog-to-digital (AD) conversion. The radiation imaging apparatuses are used, for example, as medical digital imaging apparatuses.

For image diagnosis that communicate wirelessly, radiation imaging apparatuses that capture still images, such as general radiography, and capture moving images, such as fluoroscopy, have also been developed in recent years. The radiation imaging apparatuses transmit images via wireless communication, where the portability of the radiation imaging apparatuses is improved and imaging at various locations can be made possible without the imaging location being limited to, for example, imaging rooms. Japanese Patent Application Laid-Open No. 2018-164161 discusses a technique for selecting optimum antennas based on a received signal strength indicator (RSSI) in implementing multi-input multi-output (MIMO) communication using a plurality of antennas.

When the antennas to be used for wireless communication are dynamically switched as discussed in Japanese Patent Application Laid-Open No. 2018-164161, an antenna that is not optimum can be selected due to variations in an RSSI value. This can cause downtime with a drop in usability until the antennas are selected again and switched to optimum ones. What is needed is a radiation imaging apparatus that can select an antenna capable of stable wireless communication from a plurality of antennas of the radiation imaging apparatus.

SUMMARY

A radiation imaging system includes a radiation imaging apparatus including a plurality of antennas for wireless LAN communication used in transmitting a radiation image obtained by radiation imaging and a control apparatus that controls the radiation imaging apparatus, wherein the control apparatus is configured to obtain information about the radiation imaging system, determine at least one antenna from among the plurality of antennas as an antenna to be used for the wireless LAN communication based on the obtained information, and transmit information about the at least one antenna to be used to the radiation imaging apparatus, and wherein the radiation imaging apparatus is configured to perform the wireless LAN communication using an antenna determined based on the information about the at least one antenna to be used.

Further features will become apparent from the following description of exemplary embodiments with reference to the attached drawings.

DESCRIPTION OF THE EMBODIMENTS

Figure 1:
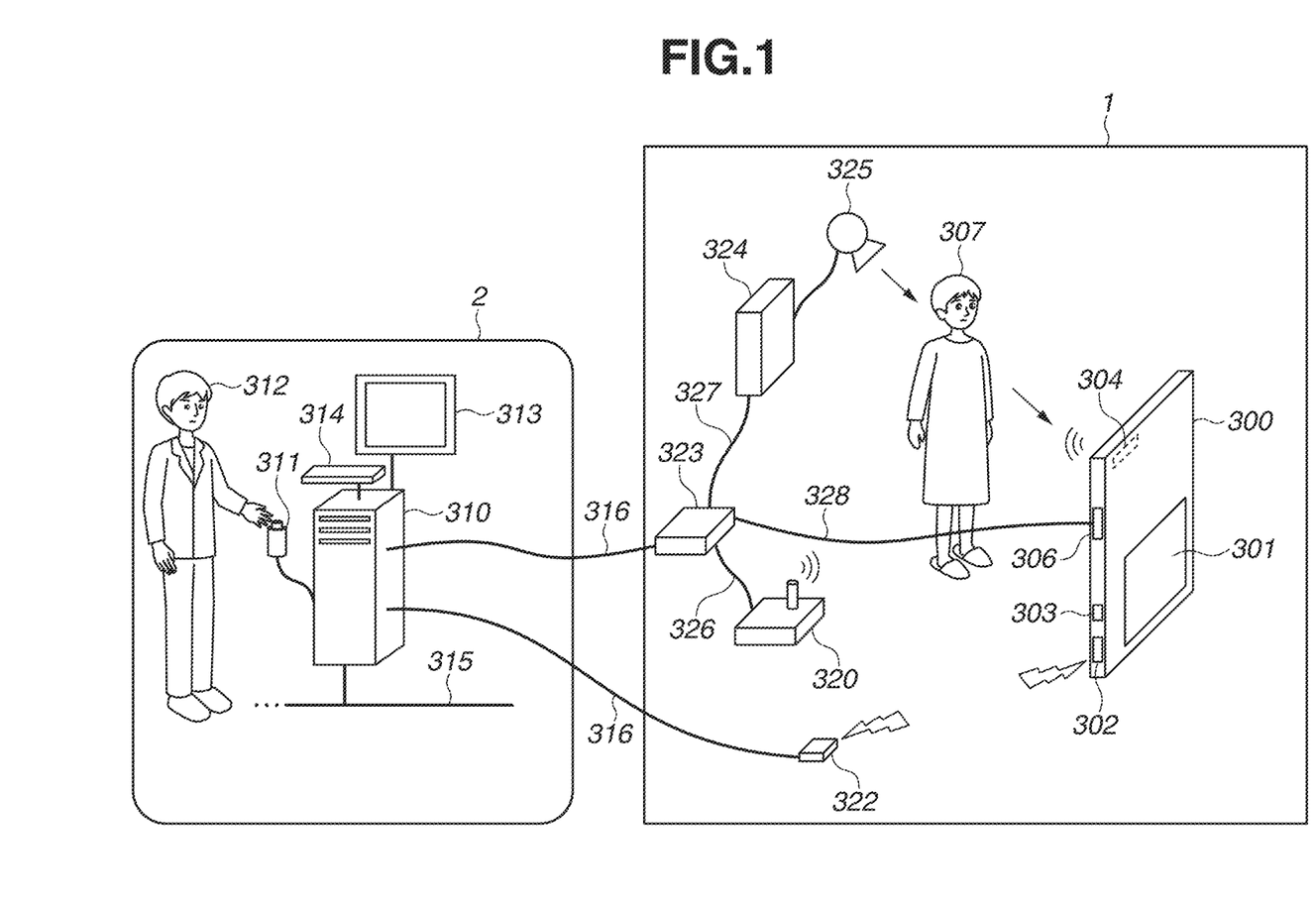
FIG. 1 is a schematic diagram illustrating a radiation imaging system according to a first exemplary embodiment.

Radiation imaging systems according to exemplary embodiments will be described below with reference to the drawings. FIG. 1 is a diagram illustrating a radiation imaging system according to a first exemplary embodiment.

As illustrated in FIG. 1, a radiation imaging system is provided in a radiation room 1 where radiation imaging using radiation irradiation is performed, and in a control room 2 located near the radiation room 1.

The radiation room 1 includes a radiation imaging apparatus 300, an access point 320, a communication control apparatus 323, a radiation generation apparatus 324, and a radiation source 325 as the radiation imaging system. The radiation room 1 also includes a communication device 322, an access point (AP) communication cable 326, a radiation generation apparatus communication cable 327, and a sensor communication cable 328. In FIG. 1, the communication device 322 is located in the radiation room 1. However, this is not seen to be limiting, and the communication device 322 can be located outside the radiation room 1.

The control room 2 includes a control apparatus 310, a radiation irradiation switch 311, a display apparatus 313, an input apparatus 314, an in-hospital local area network (LAN) 315, and radiation room communication cables 316 as the radiation imaging system.

The radiation imaging apparatus 300 includes a power supply control unit 301 including a battery and a direct-current-to-direct-current (DCDC) converter (not illustrated), a short-range wireless communication unit 302, a registration switch 303, a wireless communication unit 304, and a wired communication unit 306. The radiation imaging apparatus 300 detects radiation transmitted through a subject 307 and generates radiation image data.

The AP 320 performs wireless communication and enables the radiation imaging apparatus 300 and the control apparatus 310 to communicate via the communication control apparatus 323. The radiation imaging apparatus 300 and the communication control apparatus 323 can also perform wired communication using the sensor communication cable 328. In the present exemplary embodiment, the AP 320 uses, for example, 2.4-, 5-, or 6-GHz bandwidths of a wireless LAN.

The radiation generation apparatus 324 controls the radiation source 325 to irradiate the subject 307 with radiation.

The radiation generation apparatus 324 includes a radiation source control unit and a generation control unit (not illustrated). The radiation source control unit controls the radiation source 325 to emit radiation based on a predetermined condition. The generation control unit controls the generation of the radiation based on a signal indicating a start or stop of irradiation from the radiation imaging apparatus 300.

The radiation source control unit and the generation control unit can be configured as separate apparatuses.

The AP communication cable 326 is a cable connecting the AP 320 and the communication control apparatus 323. The radiation generation apparatus communication cable 327 is a cable connecting the radiation generation apparatus 324 and the communication control apparatus 323.

The control apparatus 310 communicates with the radiation generation apparatus 324 and the radiation imaging apparatus 300 via the communication control apparatus 323 and the AP 320 or the sensor communication cable 328, and controls the radiation imaging system.

The radiation irradiation switch 311 inputs the timing of radiation irradiation based on an operation by an operator 312. The input apparatus 314 is an apparatus for inputting instructions from the operator 312. Various input devices such as a keyboard and a touchscreen are used as the input apparatus 314.

The display apparatus 313 is an apparatus for displaying image-processed radiation image data and a graphical user interface (GUI). A display is used as the display apparatus 313. The in-hospital LAN 315 is a backbone network in the hospital. The radiation room communication cables 316 are cables connecting the control apparatus 310 with the communication control apparatus 323 and the communication device 322 in the radiation room 1.

An operation of the radiation imaging system will now be described. The operator 312 first performs an operation for registering the radiation imaging apparatus 300 in the radiation imaging system. When the operator 312 presses the registration switch 303 of the radiation imaging apparatus 300, the short-range wireless communication unit 302 of the radiation imaging apparatus 300 and the communication device 322 start short-range wireless communication therebetween.

The control apparatus 310 transmits wireless connection-related information about the AP 320 to the radiation imaging apparatus 300 via the short-range wireless communication of the communication device 322. In the case of a wireless LAN, the wireless connection-related information includes, for example, a communication method such as the Institute of Electrical and Electronics Engineers (IEEE) 802.11, a physical channel, a service set identifier (SSID), and an encryption key.

The radiation imaging apparatus 300 sets up the wireless communication unit 304 based on the received wireless connection-related information. Using this setting, the radiation imaging apparatus 300 establishes a wireless communication connection between the AP 320 and the wireless communication unit 304. The wireless connection-related information can be transmitted to the radiation imaging apparatus 300 via the sensor communication cable 328 and the wired communication unit 306.

The operator 312 then inputs subject information such as an identifier (ID), name, and date of birth of the subject 307, and an imaging site of the subject 307 into the control apparatus 310. After the input of the imaging site, the operator 312 fixes the orientation of the subject 307 and the radiation imaging apparatus 300.

With the imaging preparations completed, the operator 312 presses the radiation irradiation switch 311. When the radiation irradiation switch 311 is pressed, the radiation source 325 emits radiation toward the subject 307.

The radiation imaging apparatus 300 performs wireless communication with the radiation generation apparatus 324 to control the start and end of the radiation irradiation. The radiation irradiating the subject 307 is transmitted through the subject 307 and incident on the radiation imaging apparatus 300. The radiation imaging apparatus 300 converts the incident radiation into visible light and then detects the visible light as a radiation image signal using photoelectric conversion elements.

The radiation imaging apparatus 300 drives the photoelectric conversion elements to read the radiation image signal and converts the analog signal into a digital signal using an analog-to-digital (AD) conversion circuit to obtain digital radiation image data. The obtained digital radiation image data is transferred from the radiation imaging apparatus 300 to the control apparatus 310.

The control apparatus 310 performs image processing on the received digital radiation image data. The control apparatus 310 displays a radiation image based on the image-processed radiation image data on the display apparatus 313.

The control apparatus 310 functions as an image processing apparatus and a display control apparatus.

Figure 2:
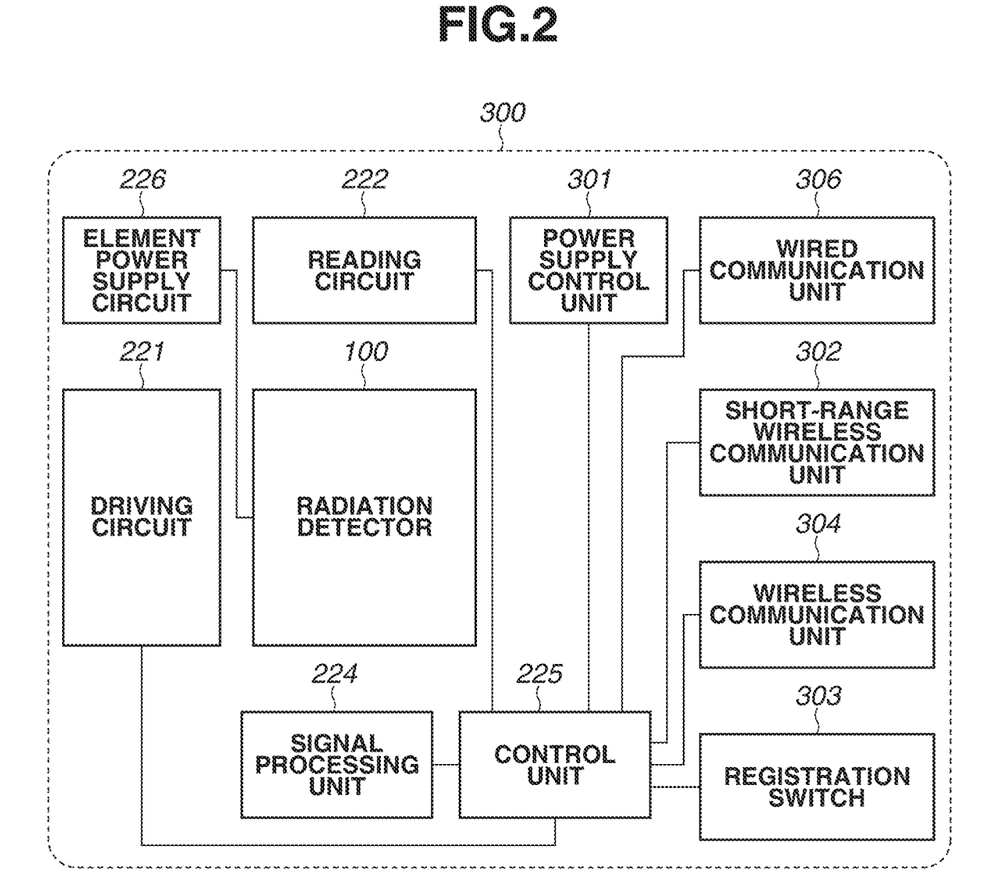
FIG. 2 is a functional block diagram of a radiation imaging apparatus according to the first exemplary embodiment.

FIG. 2 is a diagram illustrating the radiation imaging apparatus 300.

As illustrated in FIG. 2, the radiation imaging apparatus 300 includes a radiation detector 100. The radiation detector 100 has a function of detecting irradiated radiation. The radiation detector 100 includes a plurality of pixels arranged in a plurality of rows and a plurality of columns (not illustrated). In the following description, a region where the plurality of pixels is arranged in the radiation detector 100 will be referred to as an imaging region.

The radiation detector 100 includes a plurality of signal lines and a plurality of drive lines (not illustrated). Each signal line corresponds to one of the columns in the imaging region. Each drive line corresponds to one of the rows in the imaging region.

The signal lines are connected to a reading circuit 222. The reading circuit 222 includes a plurality of integration amplifiers, a multiplexer, and an AD converter. The drive lines are driven by a driving circuit 221.

The radiation detector 100 also includes bias lines (not illustrated) connected to the pixels. The bias lines receive a bias voltage Vs from an element power supply circuit 226. The bias voltage Vs is supplied from the element power supply circuit 226.

The power supply control unit 301 includes the element power supply circuit 226, and generates an analog circuit power source as well as a digital circuit power source for performing drive control and wireless communication.

A control unit 225 controls the driving circuit 221 and the reading circuit 222 based on information from a signal processing unit 224 and control commands from the control apparatus 310.

The radiation image data obtained by the operation of the above-described components is transferred to the control apparatus 310 via the wired communication unit 306 or the wireless communication unit 304.

Next, selection of antennas for the radiation imaging apparatus 300 to use in wireless communication will be described.

Figure 3:
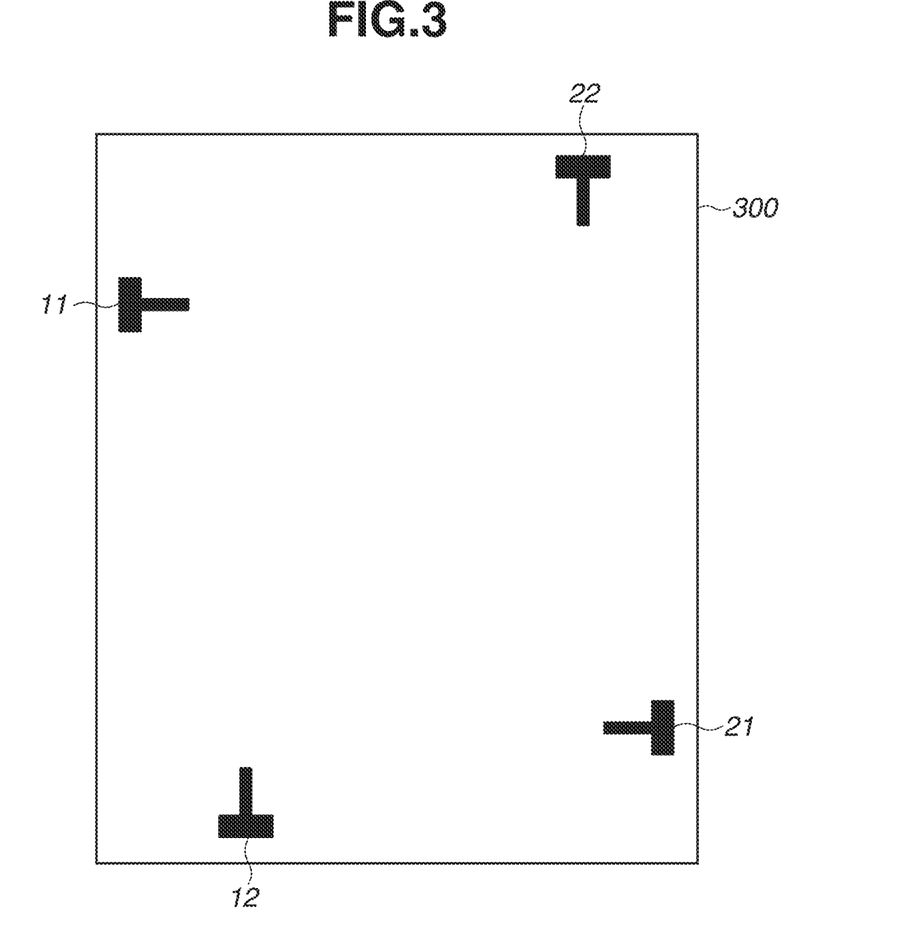
FIG. 3 is a diagram illustrating a layout example of antennas according to the first exemplary embodiment.

The wireless communication unit 304 is connected to a plurality of antennas. The wireless communication unit 304 selects several antennas from among the plurality of antennas when wirelessly communicating with the control apparatus 310. For example, as illustrated in FIG. 3, an antenna 11, an antenna 12, an antenna 21, and an antenna 22 are located at the four sides of the radiation imaging apparatus 300.

Figure 4:
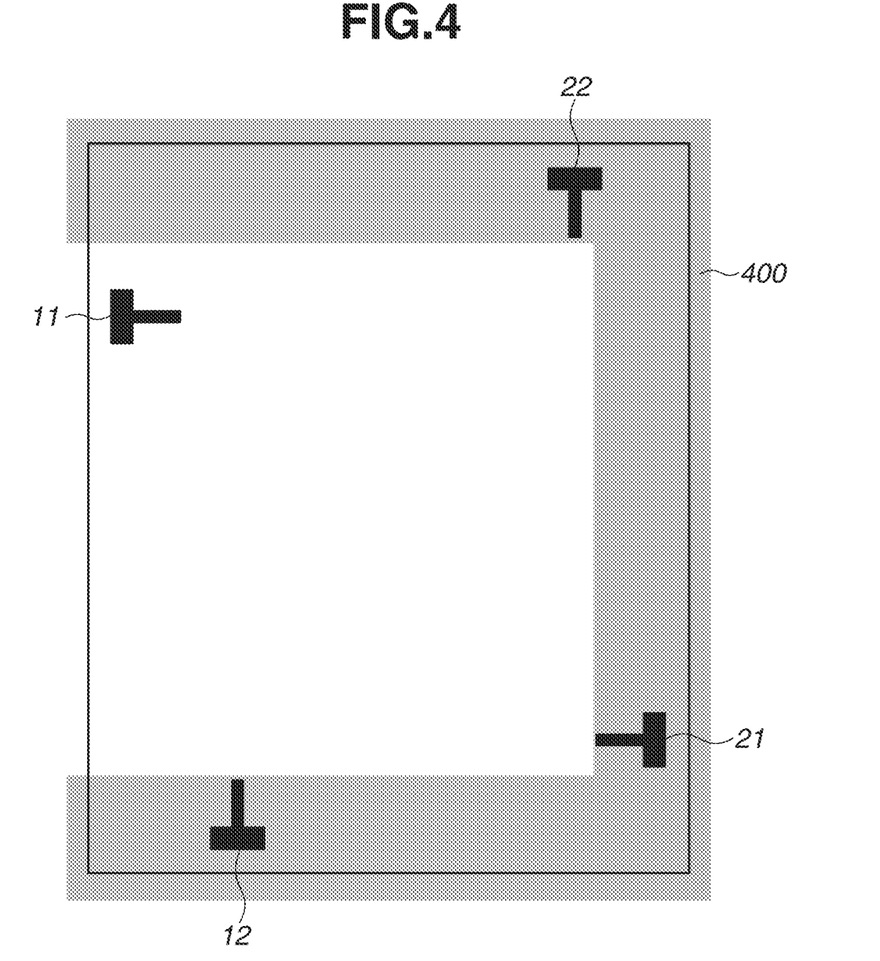
FIG. 4 is a diagram illustrating a layout example of the antennas and a Bucky housing according to the first exemplary embodiment.

In a case where the radiation imaging apparatus 300 is used in a Bucky system, the antennas other than the antenna 11 can be covered with a Bucky housing 400 as illustrated in FIG. 4. In such a case, it is difficult for the antennas other than the antenna 11 to perform good wireless communication. The control apparatus 310 therefore makes a setting to select the antenna 11 if the radiation imaging apparatus 300 is used in a Bucky system.

As described above, if the radiation imaging apparatus 300 is used in a situation where, for example, a housing where the radio waves from the antennas are shielded is known in advance, an unshielded antenna or antennas are selected from among the plurality of antennas of the radiation imaging apparatus 300. While a Bucky system is described in the foregoing example, antennas can be similarly selected in a system where the radiation imaging apparatus 300 is located in a housing such as an imaging bed.

More specifically, the control apparatus 310 selects at least one of the antennas as the antenna(s) for the radiation imaging apparatus 300 to use in wireless communication based on information about the radiation imaging system where the radiation imaging apparatus 300 is used. The information about the antenna(s) to be used is transmitted from the control apparatus 310 to the radiation imaging apparatus 300. Alternatively, the information about the radiation imaging system can be transmitted from the control apparatus 310 to the radiation imaging apparatus 300, and the radiation imaging apparatus 300 can determine the antenna(s) to be used based on the information.

If the antenna 11 is subsequently determined not to be optimum based on wireless communication information such as a received signal strength indicator (RSSI), a signal-to-noise ratio (SNR), a data rate, and the number of wireless devices using the frequency band, the antenna(s) to be used can be changed based on the wireless communication information.

The location of the radiation imaging apparatus 300 can be identified by using a known positioning technique (for example, a camera, an acceleration sensor, or the Global Positioning System [GPS]), and shielded antennas of the radiation imaging apparatus 300 can be estimated to determine the antenna(s) to be used. The imaging condition can be estimated from imaging information such as an imaging protocol, and the shielded antennas of the radiation imaging apparatus 300 can be estimated to determine the antenna(s) to be used.

In a case where the radiation imaging apparatus 300 is used without being installed on a specific device, for example, in a case where the radiation imaging apparatus 300 is held by the patient or a technician during use, the antennas shielded by the patient's or technician's hands are not fixed and are difficult to predict. In such case, at least one antenna, the communication condition of which is the most favorable, can be selected based on the foregoing various types of wireless communication information about the antennas instead of selecting the antenna(s) to be used in advance.

In the present exemplary embodiment, the four antennas 11, 12, 21, and 22 are described to be located at the four sides of the radiation imaging apparatus 300. However, the number and location of antennas are not limited thereto, as long as the radiation imaging apparatus 300 includes a plurality of antennas.

In the present exemplary embodiment, a Bucky system is described as the location where the radiation imaging apparatus 300 is used. However, this is not seen to be limiting. For example, an antenna or antennas in a stable communication environment can be selected from among the plurality of antennas of the radiation imaging apparatus 300 if such antennas are known in advance.

In the first exemplary embodiment, selection of the antenna(s) to be used by the wireless communication unit 304 to wirelessly communicate with the control apparatus 310 depends on the location where the radiation imaging apparatus 300 is used.

A second exemplary embodiment will now be described. The second exemplary embodiment is directed to a configuration where the control apparatus 310, when transmitting wireless connection information for the wireless communication unit 304 to wirelessly communicate with the control apparatus 310 to a radiation imaging apparatus 300, notifies the radiation imaging apparatus 300 of selection information about the antenna(s) to be used. In the following description, only differences from the first exemplary embodiment will be described. In the present exemplary embodiment, the radiation imaging apparatus 300 makes an optimum antenna setting with the control apparatus 310 based on the location of use.

Figure 5:
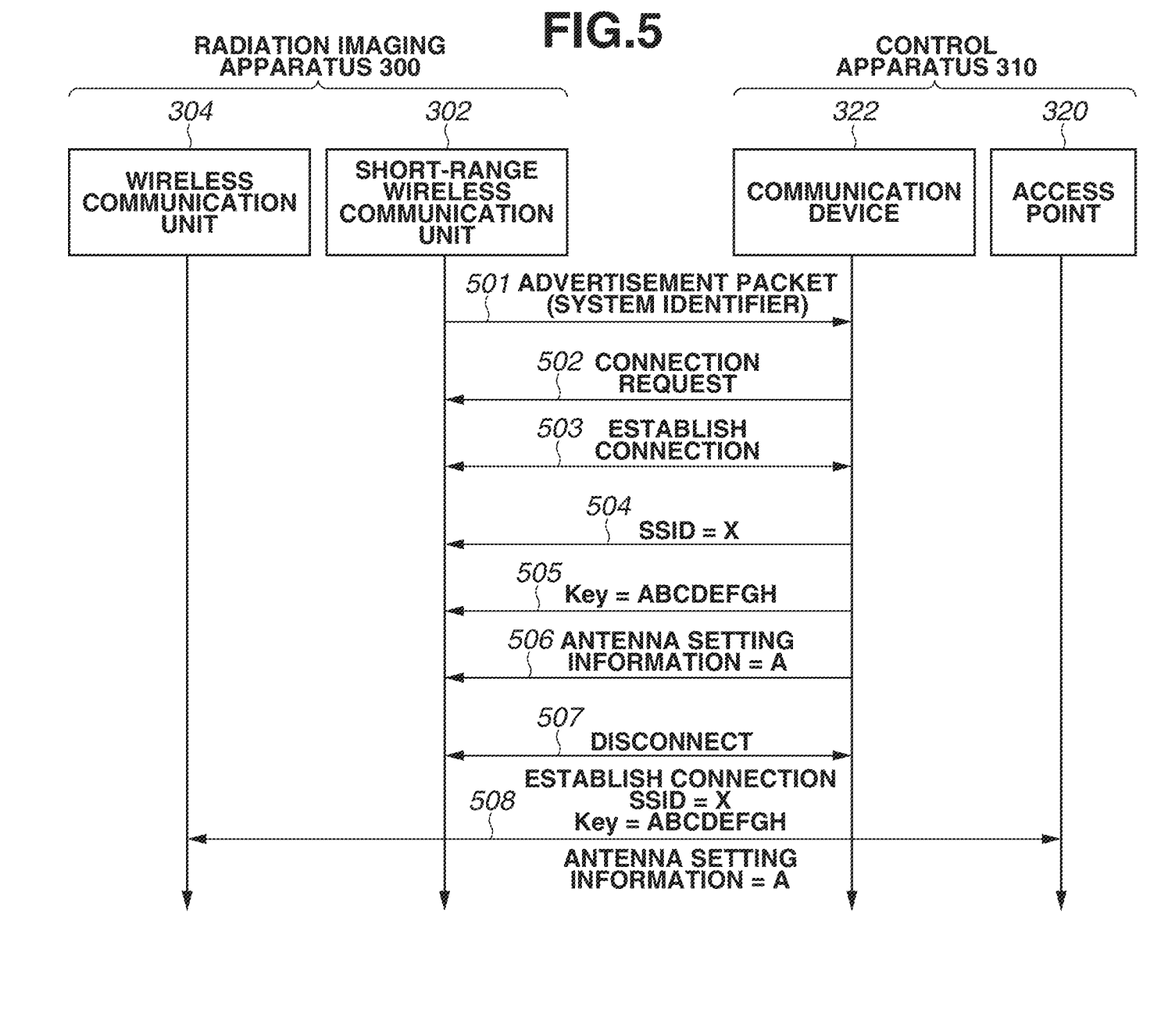
FIG. 5 is a sequence diagram illustrating an example of communication between a radiation imaging apparatus and a control apparatus according to a second exemplary embodiment.

Operations up to the establishment of connection between the wireless communication unit 304 and an AP 320 will be described with reference to the sequence diagram of FIG. 5. FIG. 5 illustrates an operation example where the radiation imaging apparatus 300 operates as a broadcaster (advertiser) to broadcast data and the control apparatus 310 operates as an observer (scanner) to monitor data.

In step 501, the radiation imaging apparatus 300, after activation, operates as an advertiser that broadcasts an advertisement packet to establish connection with the control apparatus 310. The radiation imaging apparatus 300 transmits information including a system ID to the communication device 322 using the short-range wireless communication unit 302. The communication device 322 is connected to the control apparatus 310. The transmission power during the transmission and the transmission interval of the packet can be set in advance.

The communication device 322 behaves as a scanner in a state capable of receiving an advertisement packet. If the control apparatus 310 recognizes the communication partner from the system ID received by the communication device 322 from the short-range wireless communication unit 302, the control apparatus 310 determines the signal strength based on a predetermined threshold. If the signal strength is determined to exceed the threshold, the operation of step 502 is then performed. If the signal strength is determined to not exceed the threshold, the operation of step 501 is repeated.

In step 502, the communication device 322 transmits a connection request to the short-range wireless communication unit 302. The connection request can be transmitted based on the operator's operation using an input unit of the control apparatus 310. In performing step 502, the communication device 322 enters an initiating state that is a state for starting connection. The operation of step 503 is then performed.

In step 503, the short-range wireless communication unit 302 and the communication device 322 enter a connected state. The short-range wireless communication unit 302 and the communication device 322 can perform pairing, which is sharing of encryption keys, or search for each other's services. The operation of step 504 is then performed.

In step 504, the communication device 322 transmits the SSID of the AP 320 to the short-range wireless communication unit 302 as wireless connection information. For example, the SSID is a character string "X". The SSID is desirably, but not necessarily, encrypted. The operation of step 505 is then performed.

In step 505, the communication device 322 transmits the encryption key (key) of the AP 320 to the short-range wireless communication unit 302 as wireless connection information. For example, the key is a character string "ABCDEFGH". The key is desirably, but not necessarily, encrypted. The operation of step 506 is then performed.

In step 506, the communication device 322 transmits antenna setting information to be used by the wireless communication unit 304 to the short-range wireless communication unit 302. For example, the antenna setting information is a character string "A", and includes information about the location where the radiation imaging apparatus 300 is used. The radiation imaging apparatus 300 selects at least one antenna to be used from among the plurality of antennas based on the antenna setting information.

Alternatively, the control apparatus 310 can select at least one antenna to be used based on the information about the location where the radiation imaging apparatus 300 is used, and transmit the information about the antenna(s) to be used to the radiation imaging apparatus 300 as the antenna setting information in step 506.

In the foregoing description of steps 504 to 506, the antenna setting information is transmitted after the wireless connection information (SSID and key). However, this is not seen to be limiting. The wireless connection information and the antenna setting information can be transmitted simultaneously or in succession. The order is not limited either. The operation of step 507 is then performed.

In step 507, the connection between the communication device 322 and the short-range wireless communication unit 302 is disconnected. The operation of step 508 is then performed.

In step 508, the control unit 225 controls the wireless communication unit 304 to connect to the AP 320 using the communication settings received in steps 504 and 505. The control unit 225 also controls the antenna(s) to be used by the wireless communication unit 304 based on the antenna setting information received in step 506. The AP 320 performs authentication with the new communication settings and performs communication.

The control apparatus 310 can be linked with a plurality of radiation imaging apparatuses 300. In such a case, the control apparatus 310 can individually notify each of the radiation imaging apparatuses 300 of optimum antenna settings.

Other Exemplary Embodiments

The following supplementary notes describe several aspects and selective features of the above-described exemplary embodiments.

(Supplementary Note 1)

A control apparatus configured to control a radiation imaging apparatus, the radiation imaging apparatus configured to transmit a radiation image obtained by radiation imaging via wireless communication using at least one of a plurality of antennas, wherein the control apparatus is configured to select at least one of the plurality of antennas as an antenna to be used for the wireless communication with the radiation imaging apparatus by using information about a radiation imaging system in which the radiation imaging apparatus is used, and transmit information about the antenna to be used to the radiation imaging apparatus.

(Supplementary Note 2)

The information about the radiation imaging system can be information about an environment in which the radiation imaging apparatus is used in the radiation imaging system, and the control apparatus can select at least one of antennas not shielded in the environment from among the plurality of antennas as the antenna to be used.

(Supplementary Note 3)

If the environment is one in which the radiation imaging apparatus is located in a housing, the control apparatus can select an antenna not shielded by the housing from among the plurality of antennas.

(Supplementary Note 4)

The control apparatus can transmit the information about the radiation imaging system and wireless connection information for performing the wireless communication to the radiation imaging apparatus simultaneously or in succession.

(Supplementary Note 5) The control apparatus can use different communication methods between the wireless communication and wireless communication that is different from the wireless communication and intended to communicate the wireless connection information for performing the wireless communication.

(Supplementary Note 6)

The control apparatus can use at least IEEE 802.11 or Bluetooth® in the wireless communication and the different wireless communication.

(Supplementary Note 7)

A radiation imaging system including the control apparatus according to any one of supplementary notes 1 to 6, and the radiation imaging apparatus.

(Supplementary Note 8)

A radiation imaging system configured to transmit a radiation image obtained by radiation imaging to a control apparatus by wireless communication using at least one of a plurality of antennas, wherein the radiation imaging apparatus is configured to select at least one of the plurality of antennas as an antenna to be used for the wireless communication with the control apparatus by using information about a radiation imaging system in which the radiation imaging apparatus is used.

(Supplementary Note 9)

The information about the radiation imaging system can be information about an environment in which the radiation imaging apparatus is used in the radiation imaging system, and the control apparatus can select at least one of antennas not shielded in the environment from among the plurality of antennas as the antenna to be used.

(Supplementary Note 10)

If the environment is one in which the radiation imaging apparatus is located in a housing, the radiation imaging apparatus can select at least one antenna not shielded by the housing from among the plurality of antennas as the antenna to be used.

(Supplementary Note 11) The radiation imaging apparatus can change the antenna to be used based on communication environment information about the plurality of antennas.

(Supplementary Note 12)

The communication environment information can be information about at least one of an RSSI, an SNR, a data rate, or the number of wireless devices using the same frequency band.

(Supplementary Note 13)

If an antenna shielded from among the plurality of antennas is not determinable from the information about the radiation imaging system, the radiation imaging apparatus can select at least one of the plurality of antennas as the antenna to be used based on communication environment information about the plurality of antennas.

(Supplementary Note 14)

The communication environment information can be information about at least one of an RSSI, an SNR, a data rate, or the number of wireless devices using the same frequency band.

(Supplementary Note 15)

The radiation imaging apparatus can receive the information about the radiation imaging system from the control apparatus.

(Supplementary Note 16)

A radiation imaging apparatus configured to transmit a radiation image obtained by radiation imaging to a control apparatus by wireless communication using at least one of a plurality of antennas, wherein the radiation imaging apparatus is configured to select at least one of the plurality of antennas as an antenna to be used for the wireless communication with the control apparatus based on a location where the radiation imaging apparatus is used.

(Supplementary Note 17)

A radiation imaging system including the radiation imaging apparatus according to any one of supplementary notes 7 to 16, and the control apparatus.

(Supplementary Note 18)

A control method of a radiation imaging apparatus configured to transmit a radiation image obtained by radiation imaging to a control apparatus by wireless communication using at least one of a plurality of antennas, the control method including selecting the antenna to be used for the wireless communication from among the plurality of antennas based on information about a radiation imaging system in which the radiation imaging apparatus is used.

(Supplementary Note 19)

A program for causing a computer to perform the control method according to supplementary note 18.

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)), a flash memory device, a memory card, and the like.

While exemplary embodiments have been described, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2022-117631, filed Jul. 25, 2022, which is hereby incorporated by reference herein in its entirety.

What is claimed is:

1. A control apparatus configured to control a radiation imaging apparatus in a radiation imaging system, the radiation imaging apparatus including a plurality of antennas for wireless local area network (LAN) communication used in transmitting a radiation image obtained by radiation imaging, the control apparatus comprising:
   one or more controllers configured to:
   obtain information about the radiation imaging system;
   determine at least one antenna from among the plurality of antennas as an antenna to be used for the wireless LAN communication based on the obtained information; and
   transmit information about the at least one antenna to be used to the radiation imaging apparatus.

2. The control apparatus according to claim 1,
   wherein the information about the radiation imaging system is information about an environment in which the radiation imaging apparatus is used in the radiation imaging system, and
   wherein the control apparatus is configured to select an antenna not shielded in the environment from among the plurality of antennas as the antenna to be used.

3. The control apparatus according to claim 2, wherein the information about the environment is information indicating that the environment is one in which the radiation imaging apparatus is located in a predetermined housing.

4. The control apparatus according to claim 1, wherein the control apparatus is configured to transmit the information about the radiation imaging system and wireless connection information for establishing the wireless LAN communication to the radiation imaging apparatus simultaneously or in succession.

5. The control apparatus according to claim 4, wherein the control apparatus is configured to transmit the wireless connection information to the radiation imaging apparatus via wireless communication different from the wireless LAN communication.

6. The control apparatus according to claim 5, wherein the different wireless communication is wireless communication compliant with a Bluetooth® standard.

7. A radiation imaging system comprising:
   a radiation imaging apparatus including a plurality of antennas for wireless LAN communication used in transmitting a radiation image obtained by radiation imaging; and
   a control apparatus configured to control the radiation imaging apparatus,
   wherein the control apparatus is configured to:

obtain information about a radiation imaging system that includes the radiation imaging apparatus; and determine at least one antenna from among the plurality of antennas as an antenna to be used for the wireless LAN communication based on the obtained information; and transmit information about the at least one antenna to be used to the radiation imaging apparatus, and wherein the radiation imaging apparatus is configured to perform the wireless LAN communication using an antenna determined based on the information about the at least one antenna to be used.

8. A radiation imaging apparatus, in a radiation imaging system, including a plurality of antennas for wireless LAN communication used in transmitting a radiation image obtained by radiation imaging, the radiation imaging apparatus comprising:

one or more controllers configured to:

obtain information about the radiation imaging system; and determine at least one antenna from among the plurality of antennas as an antenna to be used for the wireless LAN communication based on the obtained information.

9. The radiation imaging apparatus according to claim 8, wherein the information about the radiation imaging system is information about an environment in which the radiation imaging apparatus is used in the radiation imaging system, and wherein the one or more controllers are configured to select an antenna not shielded in the environment from among the plurality of antennas as the antenna to be used.

10. The radiation imaging apparatus according to claim 9, wherein the information about the environment is information indicating that the environment is one in which the radiation imaging apparatus is located in a predetermined housing.

11. The radiation imaging apparatus according to claim 8, wherein the one or more controllers are configured to change the antenna to be used based on communication environment information about the plurality of antennas.

12. The radiation imaging apparatus according to claim 11, wherein the communication environment information is information about at least one of a received signal strength indicator (RSSI), a signal-to-noise ratio (SNR), a data rate, or a number of wireless devices using a same frequency band.

13. The radiation imaging apparatus according to claim 8, wherein the information about the radiation imaging system is information about an environment in which the radiation imaging apparatus is used in the radiation imaging system, and wherein the one or more controllers are configured to, if an antenna shielded in the environment is not fixed from among the plurality of antennas, select at least one antenna from among the plurality of antennas as the antenna to be used based on communication environment information about the plurality of antennas.

14. The radiation imaging apparatus according to claim 13, wherein the communication environment information is information about at least an RSSI, an SNR, a data rate, or a number of wireless devices using a same frequency band.

15. The radiation imaging apparatus according to claim 8, wherein the radiation imaging apparatus is configured to receive the information about the radiation imaging system from a control apparatus of the radiation imaging system.

16. A radiation imaging apparatus including a plurality of antennas for wireless LAN communication used in transmitting a radiation image obtained by radiation imaging, the radiation imaging apparatus comprising:

one or more controllers configured to:

obtain information about a location where the radiation imaging apparatus is used; and determine at least one antenna from among the plurality of antennas as an antenna to be used for the wireless LAN communication based on the obtained information.

17. A radiation imaging system comprising:

a radiation imaging apparatus including a plurality of antennas for wireless LAN communication used in transmitting a radiation image obtained by radiation imaging, wherein the radiation imaging apparatus is configured to:

obtain information about the radiation imaging system;

determine at least one antenna from among the plurality of antennas as an antenna to be used for the wireless LAN communication based on the obtained information; and perform the wireless LAN communication using the determined antenna.

\* \* \* \* \*